United States Patent [19]

Giuliani

[11] Patent Number: 4,708,941

[45] Date of Patent: Nov. 24, 1987

[54] OPTICAL WAVEGUIDE SENSOR FOR METHANE GAS

[75] Inventor: John F. Giuliani, Kensington, Md.

[73] Assignee: The United States of America as represented by the Secretary of the Navy, Washington, D.C.

[21] Appl. No.: 709,251

[22] Filed: Mar. 7, 1985

[51] Int. Cl.$^4$ ...................... G01N 21/17; G01N 21/75
[52] U.S. Cl. .................................... 436/141; 250/227; 350/96.15; 350/96.18; 350/96.32; 356/445; 422/68; 422/83; 436/164; 436/181
[58] Field of Search ............... 436/139, 141, 164, 165, 436/167, 168, 169, 181; 422/55–60, 68, 69, 83, 86, 88, 91; 250/227; 350/96.3, 96.32, 96.15, 96.18; 356/73.1, 437, 445, 448

[56] References Cited

U.S. PATENT DOCUMENTS

| | | | |
|---|---|---|---|
| 1,022,955 | 4/1912 | Leech | 422/86 |
| 2,964,993 | 12/1960 | Witt | 250/227 X |
| 3,287,557 | 11/1966 | Bartz | 250/343 X |
| 3,315,160 | 4/1967 | Goodman | 350/96.18 X |
| 3,508,836 | 4/1970 | Polchlopek et al. | 356/246 |
| 3,513,319 | 5/1970 | Broerman . | |
| 3,528,278 | 9/1970 | Sterling | 350/96.1 X |
| 3,927,977 | 12/1975 | Jacobs | 422/86 |
| 3,957,342 | 5/1976 | Newns et al. | 350/96.30 X |
| 3,987,133 | 10/1976 | Andra | 261/131 X |
| 4,045,668 | 8/1977 | Pitt et al. . | |
| 4,050,895 | 9/1977 | Hardy et al. | 422/86 X |
| 4,063,895 | 12/1977 | Neti et al. | 422/91 X |
| 4,106,909 | 8/1978 | David et al. | 436/113 |
| 4,159,420 | 6/1979 | Tsunoda . | |
| 4,193,663 | 3/1980 | Timmermann | 350/96.18 |
| 4,270,049 | 5/1981 | Tanaka et al. . | |
| 4,352,983 | 10/1982 | Silvus, Jr. et al. . | |
| 4,367,182 | 1/1983 | Kienholz | 261/122 X |
| 4,406,843 | 9/1983 | Nakamura et al. | 261/121 R X |

FOREIGN PATENT DOCUMENTS 0391173  7/1973  U.S.S.R. ................................ 436/141

OTHER PUBLICATIONS

Felder et al., "Elementary Principles of Chemical Processes", John Wiley & Sons, New York, pp. 334–338, 1978.
Martin, "Infrared Instrumentation and Techniques", Elsever Publishing Co., pp. 155–169, 1966.
Harrick, "Internal Reflection Spectroscopy", Interscience Publishers, New York, pp. 274–279, 1967.
Kohanzadeh, J. of App. Phys., vol. 47, No. 1, pp. 177–179, 1976.
Giuliani et al., Sensors and Actuators, vol. 6, No. 2, pp. 107–112, Oct. 1984.
Giuliani et al., J. Chem. Phys., vol. 82, No. 2, pp. 1021–1024, Jan. 1985.

Primary Examiner—Barry S. Richman
Assistant Examiner—Robert J. Hill, Jr.
Attorney, Agent, or Firm—John L. Forrest; William T. Ellis; Brian C. Kelly

[57] ABSTRACT

A device for detecting small amounts of alkanes such as methane, ethane, propane, and butane gases, comprising an optical waveguide and a light source for propagating light therethrough; apparatus for obtaining samples of air to be tested; apparatus for adding water vapor to these air samples to yield gas mixtures with at least a 30% relative humidity; and means for flowing these mixtures over the surface of the optical waveguide at a rate sufficient to favor condensation of the mixture on the waveguide surface to thereby form a thin film thereon. The presence of alkanes is determined by detecting the intensity of the light after propagation through the optical waveguide and then comparing that detected intensity to a reference. In a preferred embodiment, the optical waveguide is an optical glass capillary in which the surface is closed in a lens-like configuration at the detector end.

32 Claims, 5 Drawing Figures

CROSS-SECTIONS OF WAVEGUIDE CAPILLARY

OPTICAL WAVEGUIDE SENSOR FOR METHANE GAS

BACKGROUND OF THE INVENTION

The present invention relates generally to vapor sensors, and more particularly to optical sensors for sensing alkane gases.

The development of devices for detecting toxic gases is currently an active area of research. It is highly desirable that such detecting devices be reversible, i.e., that the devices return to a baseline when the toxic gas is removed in order that the device can be reused. One such device is described in U. S. patent application Ser. No. 462,493, filed Jan. 31, 1983, entitled "REVERSIBLE OPTICAL WAVEGUIDE VAPOR SENSOR", now U.S. Pat. No. 4,513,087. This device is specifically designed to detect toxic gases such as ammonia and hydrazine. The device includes an optical waveguide, a dye film coated on the waveguide, and means for detecting a change in the optical transmittance of the waveguide. The dye film has the property of changing from its normal color to another color when it is exposed to the chemical to be detected, and then returning to its original color when the chemical is removed. The optical transmittance of the waveguide accordingly varies with the color change of the dye film coating, thereby providing an indicator which is sensitive to the presence of the chemical to be detected.

However, the above-described device is not capable of detecting explosive vapors, such as the alkane gases, because no known dyes are available which will operate to change the transmittance property of a waveguide in the presence of alkane gas. The alkane gases, such as methane, ethane, propane, and butane, are inert molecules (non-polar), and do not form an attraction to any known dye coating.

However, with the widespread use of natural gas for industrial and home heating fuel, a reliable, low cost, portable, and a sensitive leak detection system is desired. Such leak detection systems would be installed in inaccessible areas such as underground fuel lines, home and industrial furnaces, and other stations where potential natural gas leaks would provide the potential for explosions. Additionally, there is also a need for sensitive, portable, low cost, hydrocarbon detectors in the petroleum industry, where the detection of natural gas in the oceans is used to indicate the presence of oil deposits. Additionally, this type of alkanes detector is also needed in mining applications.

OBJECTS OF THE INVENTION

Accordingly, it is an object of the present invention to provide a low cost, portable alkane gas detector.

It is a further object of the present invention to provide an alkane gas detector which is reversible.

It is still a further object of the present invention to provide an optical alkane detector which does not utilize dye coatings.

Other objects, advantages, and novel features of the present invention will become apparent from the detailed description of the invention, which follows the summary.

SUMMARY OF THE INVENTION

Briefly, the above and other objects are realized by an optical detection device comprising an optical waveguide with a surface; means for propagating light through the optical waveguide; means for entraining alkanes present in a fluid to be tested within a thin liquid film on the surface of the optical waveguide; and means for detecting a parameter of the light after propagation of this light through the optical waveguide. The detecting means may include means for comparing the detected light parameter to a reference.

In a preferred embodiment, the fluid to be tested is a first gas, and the entraining means includes means for adding water vapor to the samples of the first gas to give the first gas samples at least a 30% relative humidity, and means for condensing the humidified first gas on the surface of the optical waveguide. In one embodiment, the first gas samples obtained may simply be air samples, and the water vapor adding means may simply include means for bubbling the first gas air samples through water.

DETAILED DESCRIPTION OF THE PREFERRED EMBODIMENT

The present invention is based on the fact that although the low molecular weight n-alkanes methane ($CH_4$), ethane ($C_2H_6$), propane ($C_3H_8$), and butane (n-$C_4H_{10}$) do not associate with and are nearly insoluble in water, nevertheless these gases form weak Van der Waals bonds (also termed hydrophobic bonds) with water in the gas-hydrate phase. Qualitatively, the formation of these hydrates has been attributed to the ability of the polar water molecules to surround and trap these alkanes gases in "cage-like" clathrate structures.

The principle of operation of the present alkanes detecting device is based on the above-described hydration reaction between alkane gas and water vapor when these two fluids are mixed, and the fact that this mixture will condense and produce an instantaneous liquid film on an uncoated optical waveguide surface. It has been discovered that when the condensed liquid film on the waveguide surface contains hydrated alkanes, that the transmittance of the optical waveguide is measurably affected. This change in the transmittance when hydrated alkanes are present in the condensed liquid film can then be compared to a reference value in order to determine both the presence of and the type of alkane present in a given fluid sample.

Figure 1:
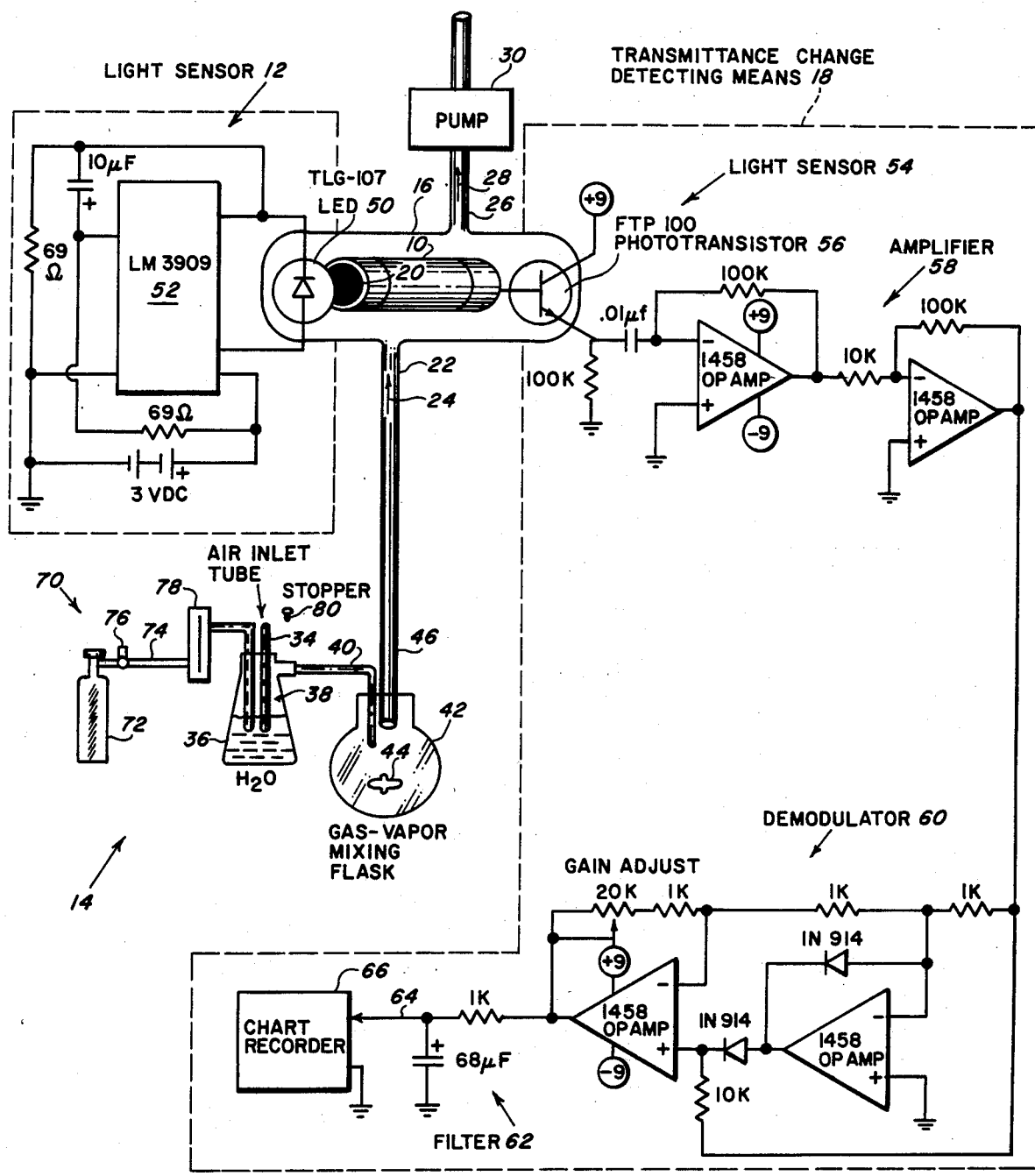
FIG. 1 is a schematic diagram of the preferred embodiment of the present invention.

Referring now to FIG. 1, there is disclosed an optical alkane vapor detector of the present invention. The device comprises an optical waveguide 10, a light source 12 for propagating light through said optical waveguide 10, apparatus 14 for obtaining a sample of a first gas, mixing water vapor with that gas and flowing it through a cell 16 surrounding the optical waveguide 10, and a transmittance change detecting means 18 for detecting the light after propagation through the optical waveguide 10 and determining the change in transmittance thereof.

The optical waveguide 10 may take a variety of forms. However, in a preferred embodiment, a capillary tube 10 is utilized. In the embodiment shown in FIG. 1, the glass capillary tube 10 has an optical stop 20 disposed at the end adjacent to the light source 12, and has its other end closed with a sealed lens-like curvature. The capillary structure is desired because only the light propagating in the outermost section of the light waveguide is of interest. Accordingly, by using a capillary tube configuration, a significantly greater number of optical reflections can be maintained between the glass-film interface close to the critical angle for total internal reflection as compared to a solid glass rod of comparable dimensions. These multiple internal reflections enhance the sensitivity of the present device by causing a large change in the light transmitted when only a small change occurs in the optical characteristics at the outer surface of the capillary tube 10. The optical stop 20 is inserted into the opening in the capillary 10 adjacent to the light source 12 in order to insure that only minimal light propagates within the hollow portion of the capillary tube 10.

The outer surface of the capillary tube 10 should be uncoated and untreated to facilitate formation of a thin aqueous film layer thereon. It is preferred that the outer surface of the capillary tube be of soda-lime glass.

As noted previously, a cell 16 surrounds the optical waveguide 10. The cell 16 includes an inlet 22 for transporting a fluid such as a gas into the cell 16 (in the direction of the arrow 24) and an outlet 26 for withdrawing the gas from the cell 16 (in the direction of the arrow 28). By way of example, the cell 16 may simply be a glass jacket. This type of cell 16 permits gas from the inlet 22 to freely circulate over the entire surface of the optical waveguide 10.

The first gas to be tested for alkanes is drawn in through the inlet 22 into the cell 16. In order to induce this flow of the first gas, some form of a pump may be placed in either the inlet line 22 or the outlet line 26 to either push or pull the gas through the cell 16. In FIG. 1, a pump 30 is shown being disposed in the outlet line 26. The pump may be operated to pulse the first gas to be tested through the cell, or to flow the first gas through in a continuous mode. The pump 30 may be implemented, by way of example, by Pump No. S/N 273 made by AEROVIRONMENT, Inc., Pasedena, Calif. Such a pump may be powered by batteries.

When a gas containing sufficient water vapor is flowed over a waveguide, at a velocity which favors condensation, then the water vapor will condense to form a thin adsorbed liquid film on the waveguide surface. The optimum velocity used in order to cause the water vapor in the gas to condense will be determined empirically simply by trying different pump rates.

When alkanes are hydrated and entrained in the foregoing condensed thin film, then a measurable transmittance change can be detected. Accordingly, it can be seen that if a first gas to be tested for alkanes contains a sufficient amount of water vapor, then that gas can be directly flowed through the cell 16 over the optical waveguide 10 in order to form a thin film therearound to facilitate the detection process. However, if the first gas to be tested does not contain sufficient water vapor, then some form of apparatus is required in order to mix the water vapor with the first gas.

A variety of devices may be utilized in order to add water vapor to the first gas to be tested. By way of example, with air as the first gas to be tested, FIG. 1 shows an apparatus 14 including an inlet tube 34, with one end disposed in a fluid to be tested, and the other end inserted into a closed flask 36 partially filled with water. The other end of this inlet tube 34 is inserted below the surface of the water in the flask 36. Typically, the inlet tube 34 is disposed to draw in, as the first gas to be tested, air. Gas in the area 38 above the water surface in the flask 36 including water vapor is drawn out through a flask outlet line 40. The gas and water vapor drawn from the flask 36 is sufficiently mixed via normal diffusion processes such that, for most applications, it could be directly flowed over the surface of the waveguide 10. However, for best results, particularly for large flask 36 volumes, the first gas and water vapor in flask outlet line 40 should be flowed into a closed gas-vapor mixing flask 42. Typically, this gas-vapor mixing flask 42 includes some form of stirring device 44, such as a magnetic stirrer, for rotating and thereby mixing the gas and the water vapor. A mixing flask output line 46 then draws this first gas-water vapor mixture out of the mixing flask 42 and applies it to the gas inlet 22 for the cell 16.

It can be seen that when the gas mixture from flask 42 is drawn or flowed over the optical waveguide 10 at the proper velocity, then the water vapor contained in the gas mixture from the inlet 22 will condense to form a thin adsorbed liquid film on the outer surface of the optical waveguide 10. If there are any alkanes present in this gas mixture, then these alkanes will be hydrated and entrained in the thin film on the optical waveguide surface. These alkanes present in the thin film will act to change the transmittance of the light through the optical fiber 10. In essence, the hydrated alkanes in the thin film cause a change in the refractive index of that film relative to a pure film of water. This relative change in the refractive index results in a modification in acceptance angle for total internal reflection, thus varying the transmittance in the adjacent optical waveguide.

The light source 12 for propagating light in the outer walls of the light waveguide 10 may take a variety of configurations. In the embodiment shown in FIG. 1, the light source 12 may include, for example, a 560 nm light-emitting-diode 50, which is driven by a standard light flasher 52. It is desirable to utilize a light flasher to drive the LED 50 in order to reduce the probability of LED burnout, and to reduce the intensity drift in the frequency of the LED 50.

The transmittance change detecting means 18 may also be realized in a variety of configurations. However, for convenience, the transmittance change detecting means 18 is embodied in FIG. 1 by a light sensor 54 comprising a phototransistor 56, an amplifier 58 comprising a set of series-connected OP AMPS connected to the output of the phototransistor 56, a demodulator 60 connected to the amplifier circuit 58, and a filter 62 connected to the output of the demodulator 60. The electronics in the present system are very similar to that disclosed in application Ser. No. 462,493, referenced previously. That application is hereby incorporated by reference.

Some means of recording this transmittance output obtained on line 64 is required. In a preferred embodiment, this recording means would also compare this transmittance output to a reference. In the embodiment shown in FIG. 1, a standard DC strip chart recorder 66 is utilized for recording the transmittance output on the line 64 and comparing that output to a baseline reference.

It should be noted that the baseline reference may be obtained simply by recording the transmittance signal level when an alkane is not present in the thin film condensed on the waveguide 10. In the alternative, a separate apparatus 70 for providing a reference gas may be provided in order to provide a reference comparison for the transmittance on line 64. This separate reference gas apparatus may simply comprise a compressed reference gas canister 72 connected via a line 74 and a valve 76 into the closed water flask 36. A flow-meter 78 may be inserted in the line 74 in order to facilitate the regulation of the amount of compressed reference gas being applied into the closed flask 36. During the time when this reference gas is being applied into the flask 36, a stopper 80 should be utilized to close the air inlet entrance of the tube 34. The stopper 80 would be utilized in order to prevent the gas or fluid to be tested from being sucked through tube 34 into the flask 36 during the reference gas flow.

The reference gas used may be simply air, or nitrogen, heluim, or any gas which is inert and will not react with the optical waveguide surface or with the alkane.

It should be noted that the above-described reference gas providing apparatus may be unnecessary in many common applications.

As an alternative to the above, a second independent optical waveguide housed in a separate cell (not shown) may be exposed to a reference gas in order to provide an instantaneous reference. This separate reference optical waveguide would also have its own transmittance change detecting means. With such a configuration, the transmittance output from this separate reference system would be applied to one input of a differential amplifier, while the transmittance output on line 64 from the optical waveguide 10 would be applied to the second input to this differential amplifier. The output from this differential amplifier would then provide an instantaneous signal which would indicate the presence or absence of alkanes in the gas under test. This signal could be connected to some form of alarm means.

As yet another alternative to the foregoing, a signal indicating the presence or absence of alkanes in a gas under test could be obtained simply by applying the signal on line 64 to one input of a differential amplifier, and applying a reference voltage to the other input of the differential amplifier in order to obtain a comparison signal therefrom. This comparison signal could then be applied to activate an alarm-type system when its voltage reached a predetermined level.

It should be noted that the electronics for the foregoing system may be implemented simply by conventional integrated circuits occupying a few square inches of space on a small printed circuit board, and may be battery-powered. The simplicity and ruggedness of such an apparatus is appropriate for portable applications.

In operation, a gas to be tested is drawn into the inlet tube 34 and into the water containing flask 36. This gas under test, after bubbling to the surface of the water in the flask 36, is drawn through the tube 40 along with water vapor and into a mixing flask 42. The gas under test and the water vapor is mixed in the flask 42 and then is drawn up through the tube 46 to the inlet 22 of the cell 16. This first gas under test with the mixed water vapor is then flowed over the optical waveguide 10 at a sufficient velocity (empirically determined) to favor condensation on the optical waveguide 10. This condensation results in an adsorbed thin liquid film on the outer surface of the optical waveguide 10. A continuous flow of this gas under test is obtained by means of the pump 30 drawing gas out through the outlet 26.

Electronically, the light source 12, via the LED 50 produces 560 nm light pulses which are directed to propagate in the outer walls of the capillary optical waveguide 10. This light is multiply reflected along the inside of the circular capillary walls producing an annular light pattern at the phototransistor 56. The phototransistor 56 converts the light pulses to electrical pulses proportional to the light pulse intensity. These electrical pulses are then amplified by the amplifier 58, demodulated by the demodulator 60, smoothed by the filter 62, and then recorded as a direct current signal via the chart recorder 66.

Figure 2:
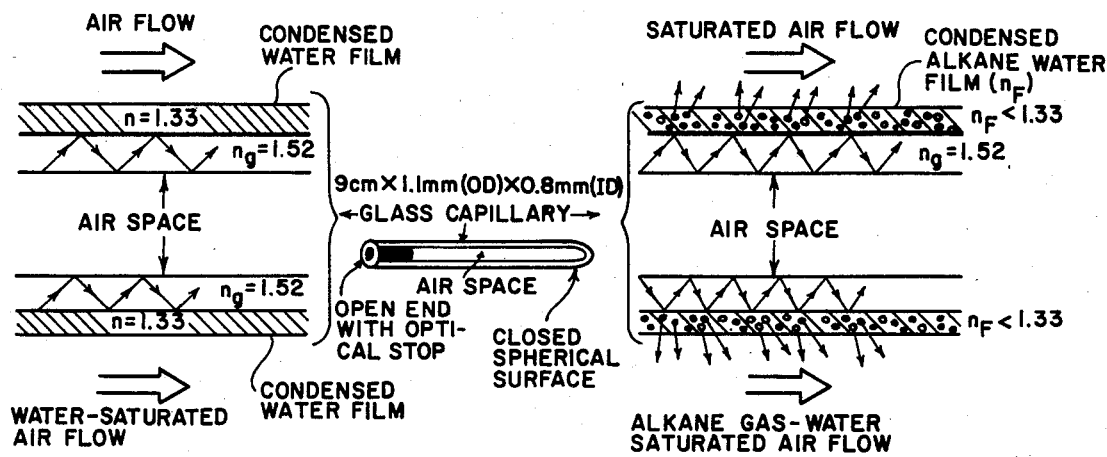
FIG. 2 is a schematic representation of a glass capillary with a condensed water film and a glass capillary with a condensed alkane-water film.

When no alkanes are present in the gas under test, only a condensed film of water is formed on the outer surface of the optical waveguide 10. This situation is shown in FIG. 2 in the representation of the glass capillary on the left hand side of the figure. The glass capillary walls are shown as having an index of refraction $n_g = 1.52$. The condensed water film is shown as having an index of refraction of 1.33.

When hydrated alkanes are present in the condensed thin film on the outer surface of the optical waveguide 10, then the refractive index of this alkane-water film decreases relative to the pure water film, i.e., $n_F < 1.33$, where $n_F$ is the refractive index of the hydrated alkane film. This decrease in the refractive index results in an increase in the acceptance angle for total internal reflection, thus intensifying the transmittance. This situation is shown in FIG. 2 in the glass capillary represented on the right hand side of the figure.

The basic surface reaction for the present device can be qualitativily described using the example of methane gas as follows:

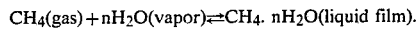

$$CH_4(gas) + nH_2O(vapor) \rightleftharpoons CH_4 \cdot nH_2O(liquid\ film).$$

It has been discovered that the humidity of the gas under test should be on the order of 30% or greater in order to allow the proper hydration of the alkane molecules into the thin film on the optical waveguide 10. It should be noted that the preferred surface for condensing this alkane-water film is soda-lime glass.

In an actual experiment to test the foregoing apparatus, methane gas of 99.5% purity from a compressed gas cylinder, at a gauge pressure of 7 psi was bubbled at 300 ml/min. into the water flask 36 containing distilled water. The water-saturated methane gas from flask 36 was drawn into the dry air mixing flask 42 by an aspirator-driven flow system, wherein it was thoroughly mixed before being drawn into the cell 16. The cell 16 had an approximate dead volume of 50 ml for housing the optical waveguide 10. This approximate 300 ml/min. flow was experimentally shown to produce a stable adsorbed film on the outer surface of a soda-lime glass capillary 10. This experiment was run at atmospheric pressure and a room temperature of 20°–22° C.

The actual sequence of experimental steps was as follows: first, dry air was drawn into the detection system to provide a zero baseline voltage on the DC strip chart recorder 66. Next, the water vapor saturated air was drawn into the cell 16 with the water vapor at 80% relative humidity at the flow rate of 300 ml/min. This produced an additional change in the recorder baseline transmittance. This baseline change in transmittance was due to the adsorption of a homogenous aqueous layer with a refractive index of 1.33 onto the outer surface of the optical waveguide capillary 10. Finally, the methane gas mixed with the water saturated air (approximately 80% relative humidity) was drawn into the cell 16 and a further shift in the recorder baseline transmittance was realized caused by the change in the index of refraction of the gas-hydrated film formed on the optical waveguide 10. It was found that this alkane-water film produced a significant increase in the optical transmittance due to the methane gas entrained within the thin surface water film. It was also experimentally shown that admitting the methane gas alone, under relatively dry air conditions (approximately 2–30 percent relative humidity) produced no detectable change above the dry air baseline.

Figure 3:
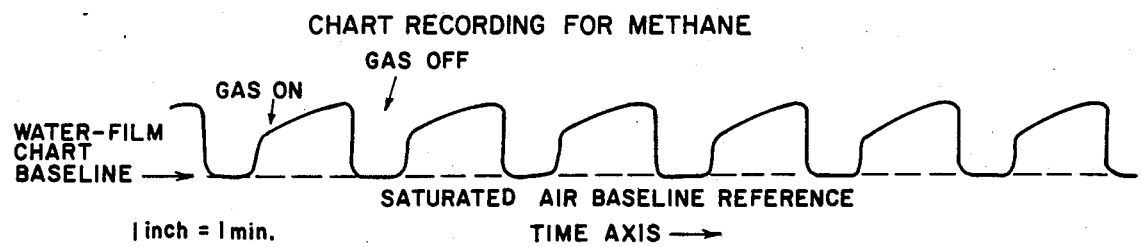
FIG. 3 is a representation of a chart recording for methane.

FIG. 3 illustrates a chart recording for methane wherein the methane from a compressed air canister is periodically turned off, and then on. A flow rate of less than 0.5 liters per minute of methane-saturated air alternating with saturated air was used at room temperature. It can be seen that the transmissivity response of the device essentially tracks this turning on and then off of the methane gas. The optical transmittance returns to the water film baseline whenever the alkane gas is removed from the cell 16. Thus, it can be seen that this process is reversible.

Figure 4:
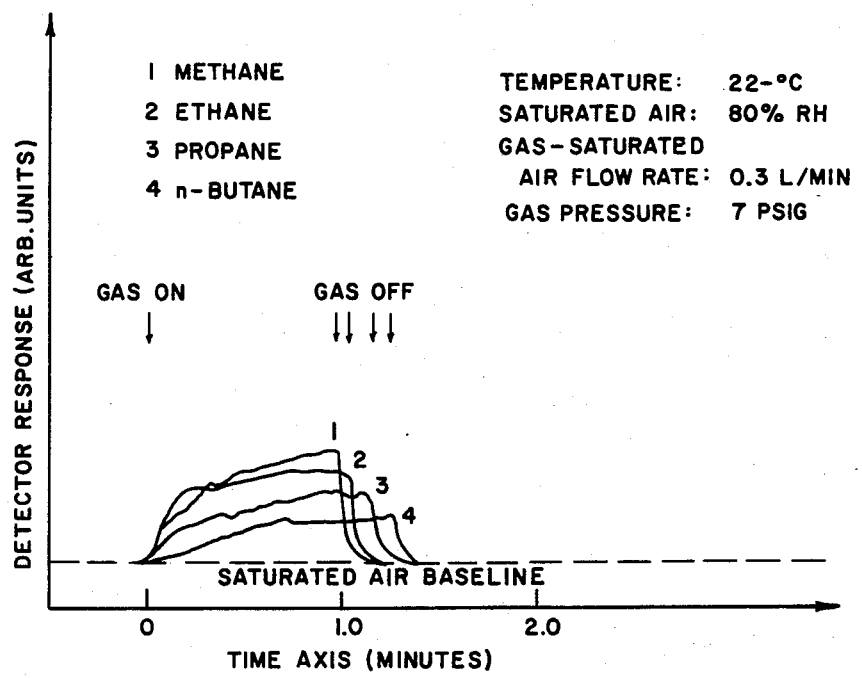
FIG. 4 is a graphical representation of the optical detector response -vs- time for the gases methane, ethane, propane, and n-butane.

As noted previously, the increase in the signal level when the hydrated methane is entrained in the thin film around the optical waveguide 10 arises due to the decrease in refractive index of that alkane-water film relative to the pure water film. This decrease in refractive index results in an increase in acceptance angle for total internal reflection, thus intensifying the transmittance. The detector response -vs- time for a variety of alkane gases is shown in FIG. 4. Because methane is the smallest molecule in this alkane series, it produces very little optical scattering. Accordingly, methane produces the greatest change in transmittance over the water-saturated air baseline in the figure. The change in transmittance response for ethane, propane, and n-butane progressively decreases relative to methane. This systematic decrease in signal response from ethane to n-butane may be attributed to the significant increase in the size of the scattering volume of these alkane hydrates relative to methane in this homologous series. In essence, as the alkane molecules increase in size, the Rayleigh scattering increases in significance. Accordingly, the light scattering losses increase with the size of the hydrated alkane and thus decrease the amount of light transmitted in the optical waveguide 10. In view of this scattering phenomena, it may be possible to increase the sensitivity of the device by probing at longer wavelengths in order to decrease the Rayleigh scattering effect. However, in the present experiment, unpolarized 660 nm and 560 nm LED light sources were used (red and green).

Figure 5:
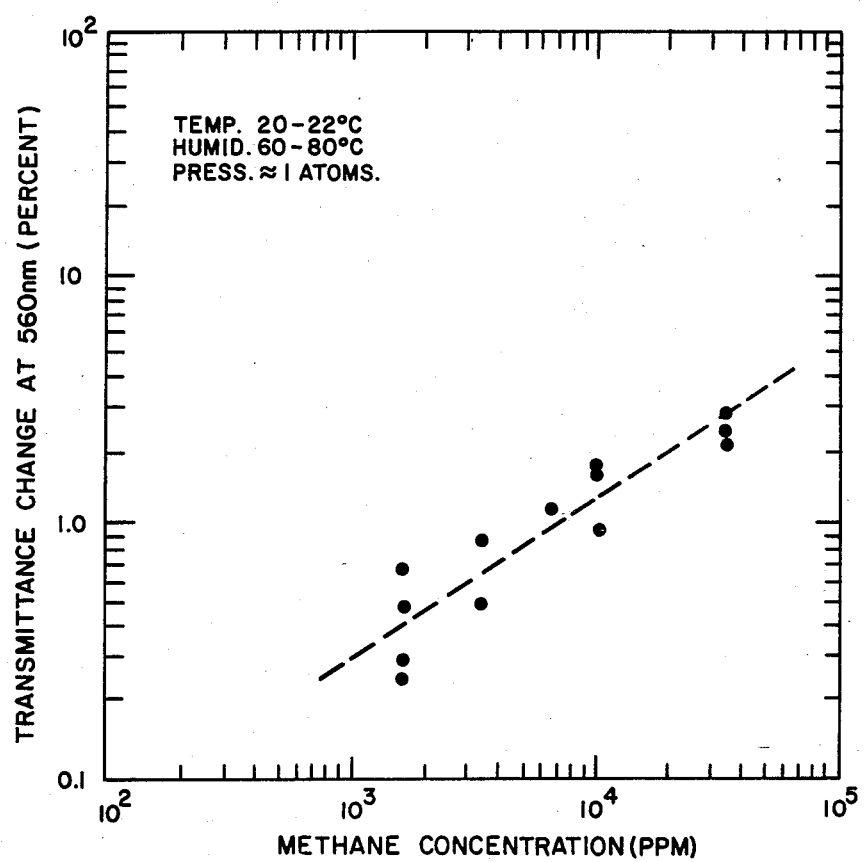
FIG. 5 is a graph of the transmittance change of an optical capillary -vs- methane concentration.

The data shown in FIG. 4 was obtained for adsorbed alkane-water thin films in equilibrium with a water-saturated hydrocarbon vapor. If this alkane gas is diluted with water-saturated air to incrementally reduce its concentration, the transmittance change -vs- the alkane concentration relationship can be obtained. Such a transmittance change -vs- alkane gas concentration is shown in FIG. 5 for methane. Essentially, fixed amounts of methane gas were injected into the water flask 36 in order to determine the sensitivity of the device. The logarithm of the transmittance in percent for a 560 nm (green) LED -vs- the logarithm of the methane gas concentration is shown for a typical set of experimental conditions, i.e., 60–80% relative humidity, at atmospheric pressure and a temperature of 20°–22° C. It can be seen that a straight line can be drawn through the data points representing a detection range between 40,000 ppm to less than 2000 ppm. This detection range is well below the recommended critical explosion concentration for the methane-air mixture of 49,500 ppm. Accordingly, this device has practical application as an inexpensive, portable detection system for natural gas leaks in furnaces, coal mines, pipe lines, etc. . . In this regard, note that natural gas in general, contains a large proportion of methane gas in its commercial mixture.

It should be noted that the response of FIG. 4 clearly indicates that there is a specific transmissivity response for each alkane molecule in the series methane, ethane, propane, and n-butane. Accordingly, this device may be used not only to detect the presence of such explosive alkanes, but may also differentiate between these different types of alkanes. Additionally, this device may be utilized to study other non-polar interfacial clathrate hydrates, i.e., the rare gases.

The present apparatus comprises a low cost portable device with a reversible response for detecting alkanes. This device does not require either an organic or an inorganic solid film coating to be applied to the optical waveguide surface. This device is unique in that the active alkane-water thin film forms only when both water vapor and an alkane gas are present together in an air stream. Moreover, the transmittance signal for the hydrated-water film has a characteristic intensity which is specific for a given alkane at room temperature (i.e., 22° C.). This device responds rapidly (i.e., within seconds) to the presence of an alkane gas such as methane, and is reversible.

As noted previously, the optical waveguide surface should be uncoated and untreated in order to facilitate the condensation of the thin alkane-water film thereon. The device is based on a hydration reaction between an alkane and water vapor. The reaction causes a simultaneous interaction between water vapor and the alkane gas to produce a liquid film on the uncoated and untreated optical waveguide surface. In a preferred embodiment, this waveguide surface is soda-lime glass.

The experimental results for the above-described device are set forth in more detail in the papers published at American Physical Society Meeting, Mar. 1984, Detroit, Mich., Vol. 29, No. 3, page 400; "Sensors and Actuators", Vol. 6, No. 2, Dec. 1984; and J. Chem. Phys. 82(2), Jan. 15, 1985. These papers are hereby incorporated by reference into the present specification.

Obviously many modifications and variations of the present invention are possible in light of the above teachings. It is therefore to be understood that within the scope of the appended claims, the invention may be practiced otherwise than as specifically described.

What is claimed and desired to be secured by Letters Patent of the United States is:

1. A method for detecting alkanes by forming and detecting clathrate structures of alkanes in a fluid at constant temperature and pressure comprising the steps of:

propagating light into an optical capillary waveguide having two ends and a longitudinal surface at end thereof which is closed with an optical stopper and with the other end thereof sealed with a lens-like curvature;

obtaining samples of a fluid to be tested;

hydrating any alkanes present in said fluid samples to be tested to yield gas mixtures with at least 30% relative humidity;

condensing any hydrated alkanes on the surface of said optical waveguide; and detecting alkanes in the fluid to be tested by detecting a parameter of light affected by weak optical surface scattering of light at any condensed alkane-water-optical surface interfaces after propagation through said optical waveguide.

2. A method as defined in claim 1, wherein said detecting step includes the step of comparing said detected light parameter to a reference.

3. A method as defined in claim 2, wherein said fluid to be tested is a first gas; and wherein said hydrating step includes the step of adding water vapor to the samples of said first gas to give said mixtures which comprise said first gas samples with at least 30% relative humidity.

4. A method as defined in claim 3, wherein said condensing step includes the step of flowing said mixtures over the surface of said optical waveguide at a rate sufficient to favor condensation on said surface.

5. A method as defined in claim 4, wherein said sample obtaining step includes the step of obtaining first gas samples of air.

6. A method as defined in claim 5, wherein said water vapor adding step comprises the step of bubbling said first gas air samples through water.

7. A method as defined in claim 6, wherein said comparing step includes the following steps:
substituting samples of a reference gas in place of the first gas samples to be tested and performing the previously recited steps; and
comparing intensity response obtained with the first gas samples to be tested to intensity response obtained with said reference gas.

8. A method as defined in claim 6, wherein said detecting step includes the step of detecting intensity of the light propagating through said optical waveguide.

9. A method as defined in claim 8, wherein said flowing step is performed at approximately 22° C. over said optical waveguide with said surface being of glass.

10. A method for detecting alkanes by forming and detecting clathrate structures of alkanes in a fluid at constant temperature and pressure comprising the steps of:
propagating light through outer walls of an optical waveguide capillary having two ends and an uncoated surface, the propagated light being confined to the outer walls of the optical capillary;
obtaining a sample of a first gas to be tested;
adding water vapor to said first gas sanple to yield a gas mixuterwith at least 30% relative humidity;
flowing said gas mixture over the surface of said optical waveguide at a rate sufficient to favor condensation of saisd gas mixture on said surface to thereby form a thin film on said surface;
detecting intensity of light affected by weak optical surface scattering of light at any condensed alkane-water optical waveguide surface interfaces after propagation through said optical waveguide; and
detecting alkanes in the first gas to be tested by comparing said detected light intensity to a reference.

11. A method as defined in claim 10, wherein said obtaining step includes the step of obtaining a sample of air as said first gas.

12. A method as defined in claim 11, wherein said water vapor adding step comprises the step of bubbling said first gas sample through water.

13. A method as defined in claim 12, wherein said flowing step is performed at approximately 22° C.

14. A method as defined in claim 13, wherein said comparing step comprises the steps of:
substituting a sample of a reference gas in place of said first gas sample and performing the previously recited propagating, adding, flowing, and detecting steps; and
comparing intensity response obtained with said first gas sample to intensity response obtained with said reference gas.

15. An optical detection device for detecting alkanes by forming and detecting clathrate structures of alkanes in a fluid at constant temperature and pressure, comprising;
a light source;
an optical capillary waveguide having two ends and a surface, with light from the light source directed into said capillary at one end thereof which is closed with an optical stopper and with the other end thereof sealed with a lens-like curvature;
means for obtaining samples of a fluid to be tested;
means for adding water molecules to the fluid samples to be tested to form gas mixtures with at least 30% relative humidity;
means for flowing the mixtures formed by said water adding means on the surface of said optical waveguide at a rate sufficient to favor condensation; and
means for detecting a parameter of light affected by a weak optical surface scattering of light at a condensed alkane-water optical waveguide surface inteface, after propagation through said otpical waveguide.

16. An alkane detection device as defined in claim 15, wherein said detecting means includes means for comparing said detected light parameter to a reference.

17. An alkane detection device as defined in claim 16, wherein the fluid to be tested is a first gas; and wherein said water molecule adding means includes means for adding water vapor to the samples of the first gas to obtain the mixtures which comprise the first gas samples having at least 30% relative humidity.

18. An alkane detection device as defined in claim 17, wherein said comparing means includes:
means for substituting samples of a reference gas in place of the first gas samples to be tested in said device; and
means for comparing the detected light parameter obtained with the first gas samples to be tested to the detected light parameter obtained with the reference gas.

19. An alkane detection device as defined in claim 17, wherein said sample obtaining means includes means for obtaining first gas samples of air.

20. An alkane detection device as claimed in claim 19, wherein said water vapor adding means includes means for bubbling the first gas air samples through water.

21. An alkane detection device as defined in claim 20, wherein said detecting means includes means for detecting intensity of light after propagation through said optical waveguide.

22. An alkane detection device as defined in claim 21, wherein said flowing means comprises apparatus for flowing the mixtures over the surface of said optical waveguide at approximately 22° C.

23. An alkane detection device as defined in claim 22, wherein said optical waveguide surface is soda-lime glass.

24. An alkane detection device as defined in claim 21, wherein said flowing means includes a gas pump.

25. An alkane detection device as defined in claim 24, wherein said water vapor adding means includes mixing means for mixing the first gas air samples after they have been bubbled through water.

26. An alkane detection device as defined in claim 24, wherein said comparing means comprises a chart recorder.

27. An alkane detection device as defined in claim 24, wherein said comparing means includes:
   means for substituting samples of a reference gas in place of the first gas air samples to be tested in said device; and
   means for comparing intensity response obtained with the first gas air samples to be tested to intensity response obtained with the reference gas.

28. An optical detection device for detecting alkanes by forming and detecting clathrate structures of alkanes in a fluid at constant temperature and pressure, comprising:
   a light source;
   an optical capillary waveguide having two ends and a longitudinal surface, with light directed into said capillary at one end thereof which is closed with an optical stopper and with the other end thereof sealed with a lens-like curvature;
   means for sampling a first gas to be tested to obtain first gas samples;
   means for adding water vapor to the first gas samples to yield gas mixtures with at least a 30% relative humidity;
   means for flowing the mixtures formed by said water adding means over the surface of said optical waveguide at a rate sufficient to favor condensation of the mixtures on said surface to thereby form a thin film on said surface;
   means for detecting intensity of light affected by weak optical surface scattering of the light at a condensed alkane-water optical waveguide surface interface after propagation through said optical waveguide; and
   means for comparing the detected light intensity to a reference.

29. An optical detection device as defined in claim 28, further including means for sampling air.

30. An optical detection device as defined in claim 29, wherein said longitudinal surface of said optical waveguide is soda-lime glass.

31. A optical detection device as defined in claim 30, wherein said flowing means includes a mixing apparatus for mixing the first gas samples after they have been bubbled through water.

32. An optical detection device as defined in claim 31, wherein said comparing means includes:
   means for substituting a sample of a reference gas in place of the first gas samples in said device; and
   means for comparing intensity response obtained with the first gas samples to intensity response obtained with the reference gas.

* * * * *